United States Patent
Alexander

(10) Patent No.: US 12,233,082 B2
(45) Date of Patent: Feb. 25, 2025

(54) COMPOSITIONS AND METHODS FOR MULTI-USE SUPPRESSION AND ACQUISITION OF VIRUSES

(71) Applicant: Ben Alexander, Minneapolis, MN (US)

(72) Inventor: Ben Alexander, Minneapolis, MN (US)

( * ) Notice: Subject to any disclaimer, the term of this patent is extended or adjusted under 35 U.S.C. 154(b) by 66 days.

(21) Appl. No.: 17/675,847

(22) Filed: Feb. 18, 2022

(65) Prior Publication Data

US 2022/0387465 A1 Dec. 8, 2022

Related U.S. Application Data

(60) Provisional application No. 63/195,710, filed on Jun. 2, 2021.

(51) Int. Cl.
| | |
|---|---|
| *A61K 31/7048* | (2006.01) |
| *A61K 31/122* | (2006.01) |
| *A61K 31/4725* | (2006.01) |
| *A61K 31/513* | (2006.01) |

(52) U.S. Cl.
CPC ........ *A61K 31/7048* (2013.01); *A61K 31/122* (2013.01); *A61K 31/4725* (2013.01); *A61K 31/513* (2013.01)

(58) Field of Classification Search
CPC .............. A61K 31/7048; A61K 31/122; A61K 31/4725; A61K 31/513
See application file for complete search history.

(56) References Cited

PUBLICATIONS

Ignacio et al. Oral and Vaginal Tenofovir for Genital Herpes Simplex Virus Type 2 Shedding in Immunocompetent Women: A Double-Blind, Randomized, Cross-over Trial. Journal of Infectious Diseases, 212(12), 1949-1956. https://doi.org/10.1093/infdis/jiv317 (Year: 2015).*

Hsiang, C.-Y., & Ho, T.-Y. Emodin is a novel alkaline nuclease inhibitor that suppresses herpes simplex virus type 1 yields in cell cultures. British Journal of Pharmacology, 155(2), 227-235. https://doi.org/10.1038/bjp.2008.242 (Year: 2008).*

Jarvis, B., & Faulds, D. Nelfinavir A Review of its Therapeutic Efficacy in HIV Infection. Adis Drug Evaluation, 56(1), 147-167. (Year : 1998).*

Marcelletti, J. F. Synergistic inhibition of herpesvirus replication by docosanol and antiviral nucleoside analogs. Antiviral Research, 56(2), 153-166. https://doi.org/10.1016/s0166-3542(02)00105-5 (Year: 2002).*

Micochova, P., Caswell, S. J., Taylor, I., Towers, G. J., & Gupta, R. K. DNA damage induced by topoisomerase inhibitors activates SAMHD 1 and blocks HIV-1 infection of macrophages. The EMBO Journal, 37(1), 50-62. https://doi.org/10.15252/embj.201796880 (Year: 2017).*

Holmes, C. B., Hallett, T. B., Walensky, R. P., Till Barnighausen, Pillay, Y., & Cohen, M. S. Effectiveness and Cost-Effectiveness of Treatment as Prevention for HIV. 91-111. https://doi.org/10.1596/978-1-4648-0524-0_ch5 (Year: 2017).*

\* cited by examiner

*Primary Examiner* — Yih-Horng Shiao
*Assistant Examiner* — Hoi Yan Lee
(74) *Attorney, Agent, or Firm* — Husch Blackwell LLP

(57) ABSTRACT

HIV pre-exposure prophylaxis (PrEP) has been available for nearly a decade. Patients can take a pill comprising of multiple antiviral agents that, if exposed to HIV, will prevent a permanent viral infection with an extremely high success rate. However, the use of PrEP antivirals has been linked to higher rates of STIs including HSV-1, HSV-2, Infectious Mononucleosis, chlamydia, gonorrhea, trichomanias, and syphilis. In particular, Herpes Simplex Viruses 1 and 2 can cause symptoms including oral or genital sores, while mono, caused by the Epstein-Barr Virus, can cause prolonged sickness. This disclosure utilizes two or more antiviral agents as a multi-use therapy for both suppressing a chronic herpesvirus infection while preventing an HIV infection. With this therapy, the odds of both acquiring HIV or spreading a herpesvirus are greatly reduced during human contact.

2 Claims, 7 Drawing Sheets

| Group # | Proposed Daily Doses for Each Study Group |
|---|---|
| 1 (Control) | Placebo |
| 2 (Traditional) | • Valacyclovir 300 mg<br>• Valacyclovir 500 mg<br>• Valacyclovir 1000 mg<br>• Pritelivir 100 mg |
| 3 (Experimental) | 1. Valacyclovir 300 mg, TDF 300 mg, Emtricitabine 200 mg<br>2. Valacyclovir 500 mg, TDF 300 mg, Emtricitabine 200 mg<br>3. Valacyclovir 1000 mg, TDF 300 mg, Emtricitabine 200 mg<br>4. Valacyclovir 300 mg, TAF 25 mg, Emtricitabine 200 mg<br>5. Valacyclovir 500 mg, TAF 25 mg, Emtricitabine 200 mg<br>6. Valacyclovir 1000 mg, TAF 25 mg, Emtricitabine 200 mg<br>7. Valacyclovir 300 mg, TDF 300 mg, Lamivudine 300 mg<br>8. Valacyclovir 500 mg, TDF 300 mg, Lamivudine 300 mg<br>9. Valacyclovir 1000 mg, TDF 300 mg, Lamivudine 300 mg<br>10. Valacyclovir 300 mg, TAF 25 mg, Lamivudine 300 mg<br>11. Valacyclovir 500 mg, TAF 25 mg, Lamivudine 300 mg<br>12. Valacyclovir 1000 mg, TAF 25 mg, Lamivudine 300 mg<br>13. Pritelivir 100 mg, TDF 300 mg, Emtricitabine 200 mg<br>14. Pritelivir 100 mg, TAF 25 mg, Emtricitabine 200 mg<br>15. Pritelivir 100 mg, TDF 300 mg, Lamivudine 300 mg<br>16. Pritelivir 100 mg, TAF 25 mg, Lamivudine 300 mg |

FIG. 4

| Test # | Test | Frequency | Measuring | Success Metric |
|---|---|---|---|---|
| 1 | HSV-1 infection site PCR | Daily | DNA copies per mL | % of days <150 copies / mL for suppression |
| 2 | HSV-2 infection site PCR | Daily | DNA copies per mL | % of days <150 copies / mL for suppression |
| 3 | Epstein Barr Virus Saliva PCR | Daily | DNA copies per mL | % of days <150 copies / mL for suppression |
| 4 | HIV Antigen/Antibody | Weekly | HIV seroconversion | Seronegative |
| 5 | Western Blot | Weekly | HSV seroconversion or detectability | HSV particles or infected cells undetectable in HSV+ patient's blood sample |
| 6 | Hair Sample | Weekly | Patient medication adherence | Median >0.023 ng/mg tenofovir in sample for 4 doses/wk Median >0.038 ng/mg tenofovir in sample for 7 doses/wk |

FIG. 5

| Group # | Proposed 2-1-1 Doses for Each Study Group |
|---|---|
| 1 (Control) | Placebo |
| 2 (Traditional) | • Valacyclovir 300 mg<br>• Valacyclovir 500 mg<br>• Valacyclovir 1000 mg<br>• Pritelivir 100 mg |
| 3 (Experimental) | 1. Valacyclovir 300 mg, TDF 300 mg, Emtricitabine 200 mg<br>2. Valacyclovir 500 mg, TDF 300 mg, Emtricitabine 200 mg<br>3. Valacyclovir 1000 mg, TDF 300 mg, Emtricitabine 200 mg<br>4. Valacyclovir 300 mg, TAF 25 mg, Emtricitabine 200 mg<br>5. Valacyclovir 500 mg, TAF 25 mg, Emtricitabine 200 mg<br>6. Valacyclovir 1000 mg, TAF 25 mg, Emtricitabine 200 mg<br>7. Valacyclovir 300 mg, TDF 300 mg, Lamivudine 300 mg<br>8. Valacyclovir 500 mg, TDF 300 mg, Lamivudine 300 mg<br>9. Valacyclovir 1000 mg, TDF 300 mg, Lamivudine 300 mg<br>10. Valacyclovir 300 mg, TAF 25 mg, Lamivudine 300 mg<br>11. Valacyclovir 500 mg, TAF 25 mg, Lamivudine 300 mg<br>12. Valacyclovir 1000 mg, TAF 25 mg, Lamivudine 300 mg<br>13. Pritelivir 100 mg, TDF 300 mg, Emtricitabine 200 mg<br>14. Pritelivir 100 mg, TAF 25 mg, Emtricitabine 200 mg<br>15. Pritelivir 100 mg, TDF 300 mg, Lamivudine 300 mg<br>16. Pritelivir 100 mg, TAF 25 mg, Lamivudine 300 mg |

FIG. 6

| Test # | Test | Frequency | Measuring | Success Metric |
|---|---|---|---|---|
| 1 | HSV-1 infection site PCR | Daily during 2-1-1 | DNA copies per mL | % of days <150 copies / mL for suppression |
| 2 | HSV-2 infection site PCR | Daily during 2-1-1 | DNA copies per mL | % of days <150 copies / mL for suppression |
| 3 | Epstein Barr Virus Saliva PCR | Daily during 2-1-1 | DNA copies per mL | % of days <150 copies / mL for suppression |
| 4 | HIV Antigen/Antibody | Weekly | HIV seroconversion | Seronegative |
| 5 | Western Blot | Weekly | HSV seroconversion or detectability | HSV particles or infected cells undetectable in HSV+ patient's blood sample |
| 6 | Hair Sample | Weekly | Patient medication adherence | Median >0.023 ng/mg tenofovir in sample for 4 doses/wk Median >0.038 ng/mg tenofovir in sample for 7 doses/wk |

FIG. 7

COMPOSITIONS AND METHODS FOR MULTI-USE SUPPRESSION AND ACQUISITION OF VIRUSES

CROSS-REFERENCE TO RELATED APPLICATION

This application claims the benefit and priority of U.S. Provisional Application No. 63/195,710, filed Jun. 2, 2021, the contents of which are hereby incorporated by reference in their entirety herein.

TECHNICAL FIELD

The present disclosure generally relates to treatment of viral infections. In particular, the present disclosure relates to compositions of one or more antiviral drugs for suppressing human herpesvirus (HHV) and preventing acquisition of human immunodeficiency virus (HIV).

BACKGROUND

Presently, there are two primary variants of HIV and nine distinct herpesviruses that infect humans. Once acquired, an untreated HIV infection dramatically shortens the lifespan of a patient. A herpes infection presents recurrent symptoms and lasts for life. HIV integrates into the DNA of T cells, crippling the immune system. Herpesviruses lie dormant in the nerve cells of mammals, reactivating from several triggers which include stress, sun exposure, sleep deprivation, or depression of the immune system. When reactivated, herpesviruses may present recognizable symptoms including sores around the mouth or genitals, fatigue, fever, aches, rashes, and a variety of other ailments. HIV infections may enter a dormant period of weeks to years after primary infection, eventually overwhelming a patient.

Natural immunity to HIV exists in the form of T cells lacking the CCR5 surface proteins that HIV attach to. This trait, CCR5-delta 32, evolved as a selective pressure from the plagues of the Middle Ages, yet it is exceedingly rare (Duncan et al., 2005). Manufactured immunity comes in the form of modern pharmaceuticals. Oral Pre-exposure Prophylaxis, or PrEP, contains two drugs in the class of nucleoside/nucleotide reverse transcriptase inhibitors (NRTIs). NRTIs substitute themselves for viral nucleotides in the HIV replication process, causing chain termination. In chain termination, the DNA strand being built is truncated, therefore stopping viral replication in the cell. While these antivirals are used to suppress an active HIV infection, when taken prophylactically, they can prevent a permanent HIV infection when exposed to the virus.

In the case of herpesviruses, most are acquired from parents in childhood. A herpesvirus infection may present no symptoms at all, implying the host's immune system can defend from the worst effects of the chronic disease. However, the herpesvirus is still replicating inside of the host, and the host is still highly contagious. Herpes simplex 1 is PCR detectable on the surface tissues of humans on average 19.7% of the time (Ramchandani et al., 2016). It is this asymptomatic shedding, rather than when symptoms present, that herpesviruses are most likely to spread to other humans, highlighting the need for continuous antiviral therapy.

Herpesviruses infections can increase comorbidities. In immunocompromised patients, such as HIV positive patients, those receiving immunosuppressant therapy, or patients who have had organ transplants, herpes infections can cause more severe disease. Patients seropositive for herpes simplex virus 2 are at a 2-4 fold increased risk of acquiring HIV (Anuradha et al., 2008). Herpes simplex 1 is receiving attention as a potential causal agent in Alzheimer's disease (Cairns et al., 2020). Unaddressed or improperly treated herpes infection presents severe risks to negative lifelong patient outcomes.

Presently, there are few treatment options for herpesvirus infections. In the case of genital herpes from HSV-1 and HSV-2, untreated, asymptomatic cases shed viral particles and contribute to transmission (Sen et al., 2007). The most common treatment for a herpes infection is the administration of a single antiviral agent such as valacyclovir, acyclovir, pritelivir, famciclovir, or acyclovir when symptoms appear, and only for a period of days in conjunction with symptoms. However, patients are still highly infectious while presenting symptoms, despite being on antiviral therapy. Therefore, novel treatments must provide better patient outcomes in suppressing not only symptoms, but suppressing the virus and transmission entirely.

Existing therapies are not always effective at treating chronic herpes infections, they allow for the possibility of mutations leading to drug-resistant variants of herpes. When a herpes virus reactivates, triggering infectious mononucleosis in the case of Epstein-Barr virus, also known as human herpesvirus 4, or sores in the case of HSV-1 and HSV-2, the viral load in a patient exponentially increases. When a single nucleoside/nucleotide analog is taken only during an outbreak, the high viral load, combined with a selective pressure from the antiviral, leads to the development of resistant herpes variants over time. The most likely herpes mutation to occur is in the DNA polymerase enzyme of the herpesvirus. This causes resistance to valacyclovir, acyclovir, and other nucleoside/nucleotide analog class drugs.

With traditional antiviral therapy for herpesviruses, nucleoside/nucleotide analogs such as acyclovir, famciclovir, tenofovir and salt forms thereof (examples include tenofovir disoproxil fumarate (TDF) and tenofovir alafenamide (TAF)), valacyclovir, or another single nucleoside/nucleotide analog, block herpesvirus DNA polymerase by substituting themselves for the traditional building blocks or nucleotides of DNA, causing chain termination. However, by taking a single antiviral agent, there is evolutionary selective pressure for the herpesvirus to develop chance mutations that incur antiviral resistance. Given time, mutations in the herpesvirus's 130,000-250,000 genetic base pairs of DNA will create a virus variant more resistant to antiviral therapy. Taking one antiviral agent at peak viral loads, such as during an outbreak, only increases the chances of resistance mutations to occur.

In the case of nucleoside/nucleotide analogs, this resistance results from changes to the herpesvirus DNA polymerase or HIV reverse transcriptase enzyme. The mutated DNA polymerase or reverse transcriptase enzyme confers resistance by preferring DNA nucleotides over the fake antiviral nucleoside/nucleotide analogs that cause chain termination. By rejecting the antiviral agent in its replication, the virus develops immunity to the therapy, resulting in an infection that is harder to treat. In HIV therapy, this behavior is well known, and therapy accounts for these potential mutations. For herpesviruses, however, Acyclovir resistant strains already account for 0.3% of existing human HSV-1 and HSV-2 infections, in part due to the resistance process listed above (Danve-Szatanek et al., 2004). Furthermore, patients could acquire a strain of acyclovir resistant herpes without ever having used antiviral therapy before.

When treating or preventing HIV, the existence of vial resistance is known and accounted for. For chronic HIV, an antiviral therapy comprising at least three agents is used, more effectively suppressing the virus and preventing resistance mutations. For preventative HIV, two antiviral agents are used, again preventing acquisition at multiple points in the viral replication process. However, since most patients on PrEP are seropositive for at least one herpesvirus, additional therapies are needed to prevent HIV acquisition and suppress herpesviruses replication and transmission

SUMMARY

The included disclosure lists methods and compositions for preventing HIV acquisition in seronegative patients while suppressing viral loads in herpes seropositive patients, viruses that once infected, are lifelong diseases. An antiviral cocktail, comprising two or more antiviral agents, prevents resistance mutations while obstructing replication at phases of the viral reproductive process for both families of human immunodeficiency viruses and herpesviruses. Certain antiviral agents are used for their cross-strain protection against both HIV and herpesviruses. The antiviral agents are in the class of nucleoside/nucleotide analogs, with the other agents comprising NRTIs, DNA polymerase inhibitors, protease inhibitors, nuclease inhibitors, or other obstructors of the viral replication process.

As antiviral agents create a selective pressure on the family of presently nine human herpesviruses and two human immunodeficiency viruses to develop resistance mutations, multiple antiviral agents are used to significantly lower the likelihood of a resistant virus variants to develop from treatment. The antiviral cocktail provides cross-strain protection against multiple variants of human herpesviruses and HIV strains. The antiviral agents further decrease the likelihood of forward or reverse herpesvirus zoonotic transmission in humans who have close contact with mammals. The effective regimen can virally suppress a herpes seropositive patient to nearly or completely undetectable levels, verified by testing. Therefore, the likelihood of transmitting or acquiring an additional lifelong herpesvirus is significantly reduced with the novel antiviral cocktail. Additionally, the risk of acquisition of HIV is extremely low with the same therapy.

Conventional testing can determine if therapy is effective at dual suppression and prevention. PCR can determine if viral particles are present in a sample, in the case of a suspect HIV blood sample, herpesvirus sores, or herpesvirus asymptomatic shedding. Western Blot can detect both the presence of HIV and herpesviruses, as well as the approximate viral load based on the amount of virus proteins in the sample. IgG can detect if a patient has ever acquired a HIV or herpesvirus infection, while IgM can detect if a patient has seroconverted from HIV or herpes negative to positive (Theel, 2020).

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIG. 4 is a table depicting a dosage schedule for a proposed clinical trial measuring the efficacy of an embodiment of a composition.

FIG. 5 is a table depicting tests that can be performed to measure efficacy of the proposed clinical trial of FIG. 4.

FIG. 6 is a table depicting a dosage schedule for a proposed clinical trial measuring the efficacy of an embodiment of the composition taken on a short term or irregular basis.

FIG. 7 is a table depicting tests that can be performed to measure efficacy of the proposed clinical trial of FIG. 6.

Figure 1:
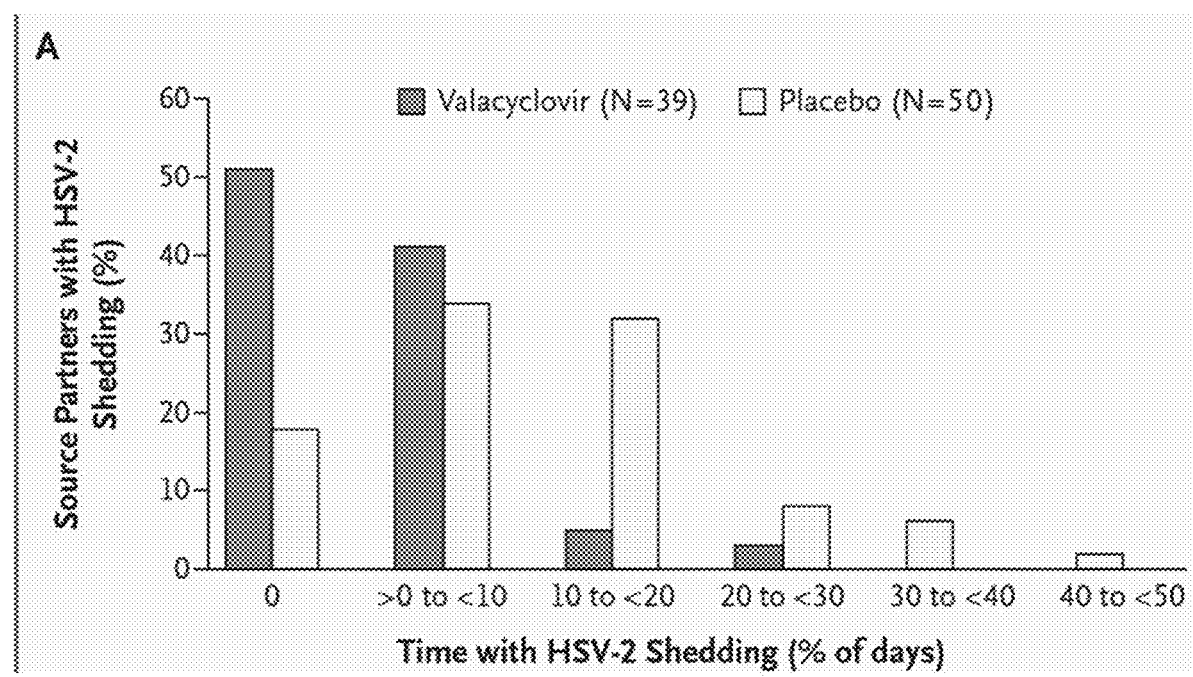
FIG. 1 is a graph depicting the efficacy of prior art HSV suppression drug valacyclovir in regards to suppressing HSV, segmented by 6 columns of % days PCR detectable shedding.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

"Asymptomatic shedding" refers to the process in which people who are infected with HSV but do not present symptoms produce infectious particles that can be transmitted to others.

"Disease" refers to an abnormal process or bodily function, caused herein by acquisition of an infectious virus.

"Disorder" refers to an illness, caused herein by an infectious disease that causes disorder within the host.

"Effective dosage" refers to the amount of the active ingredient of one or more antiviral agents needed in therapy to suppress or prevent a viral infection.

"Herpesvirus" refers to a class of viruses which establish permanent residency in the host by a dormancy stage in nerve cells.

"Human immunodeficiency virus" or "HIV" refers to a virus which establishes permanent residency by integrating its genetic code with a human host.

"Herpes simplex virus type 1", "HSV-1", or "oral herpes" refers to a type of herpesvirus which typically infects humans in the mouth and presents as cold sores.

"Herpes simplex virus type 2", "HSV-2" or "genital herpes" refers to a type of herpesvirus which typically infects humans in the genitals and presents as genital sores.

"Infection" refers to acquisition of a viral agent that establishes permanent residence within the host.

"Nucleoside analogs" or "nucleotide analogs" refer to a type of antiviral agent, substituting itself in the genetic code of a virus during replication which stops viral replication.

"Nucleoside Reverse Transcriptase Inhibitors", "NRTIs", "Nucleotide Reverse Transcriptase Inhibitors", or "NtRTIs" refer to a class of drugs used to treat HIV by blocking reverse transcriptase, an HIV enzyme, and preventing HIV replication.

"Polymerase chain reaction" or "PCR", as used herein, refers to a test that detects the presence of a virus at the time of the test. PCR can also detect fragments of a virus after the duration of clinical symptoms.

"Preexposure prophylaxis" or "PrEP" refer to a medication or method for HIV prevention in HIV-negative individuals.

"Protease inhibitors" or "nuclease inhibitors" refer to a type of antiviral agent, inserting itself in the respective enzyme of a newly formed virus, which stops viral maturation of its genetic material preventing the virus from being infectious.

"Replication" refers to a virus's means of creating copies of itself through infecting a host cell.

"Suppression" refers to use of an antiviral agent to reduce the number of viral copies present in a host.

"Suppressive therapy" refers to use of one or more antiviral agents on a frequent and consistent basis to reduce the number of viral copies in a host for a prolonged amount of time.

"Viral load" refers to a metric expressing the amount of a virus in an organism or number of viral particles per volume of fluid.

"Virus" refers to an entity comprising genetic information and enveloped by proteins which replicates via a host.

"Western Blot" or "western blotting" refers to a technique that uses antibodies to detect specific proteins in a sample.

The included disclosure describes a novel antiviral therapy for patients HIV negative and herpesvirus positive. Patients receive a therapeutically effective dose of treatment containing multiple antiviral agents, containing NRTI-class drugs, Nucleotide/Nucleoside analogs, protease inhibitors, nuclease inhibitors, or a combination thereof. There may be two, three, four, five, or six antiviral agents administered in each therapeutic dose. The antivirals are administered at a regular interval for combination suppressive and preventative therapy. The therapeutically effective dose is between 10 mg to 3000 mg of each antiviral agent, administered as each agent individually at the prescribed interval, or as a combined pharmaceutical at the prescribed interval. The interval may be daily, every other day, weekly, bi-weekly monthly, bi-monthly, or at another regular frequency that allows for effective viral suppression. The method of delivery to the patient includes intravenous or IV, oral, rectal, topical, or any other effective distribution method to the patient. The formulation of the therapy includes the substances as a series of or individual dose of a salt, solvent, powder, pill, gel, liquid, cream, shot, or other therapeutically effective formulation. The therapy includes the antiviral agents, and all associated binders, molecular delivery mechanisms, and cellular entry facilitators to effectively deliver the antiviral agents into the patient. These include the inactive ingredients in the formulation. The inactive ingredients may include cellulose, croscarmellose sodium, lactose monohydrate, magnesium stearate, corn starch, water, carnauba wax, titanium dioxide, aluminum oxide, triacetin, silicon dioxide, crospovidone, hypromelloses, polyethylene glycols, polysorbates, povidones, and other fillers, dyes, and coatings in prescription medications.

Effective HIV prevention involves a patient remaining negative for HIV via PCR, Western Blot, RNA, IgG or IgM antibody tests. Effective herpesvirus suppression involves substantially reducing the total number of viral copies of herpesvirus in a patient within days or weeks of the start of antiviral therapy i.e. after 3 weeks post treatment initiation. The reduction can be measured via conventional tests including PCR, Western Blot, IgG antibodies and IgM antibodies. When the novel antiviral therapy is effective, a patient's HIV status will remain negative for the duration of therapy. Additionally, the herpes viral load will be nearly or entirely undetectable by PCR or Western Blot, or herpesvirus antibody levels will decline over a period of days, weeks, months or years.

Figure 2:
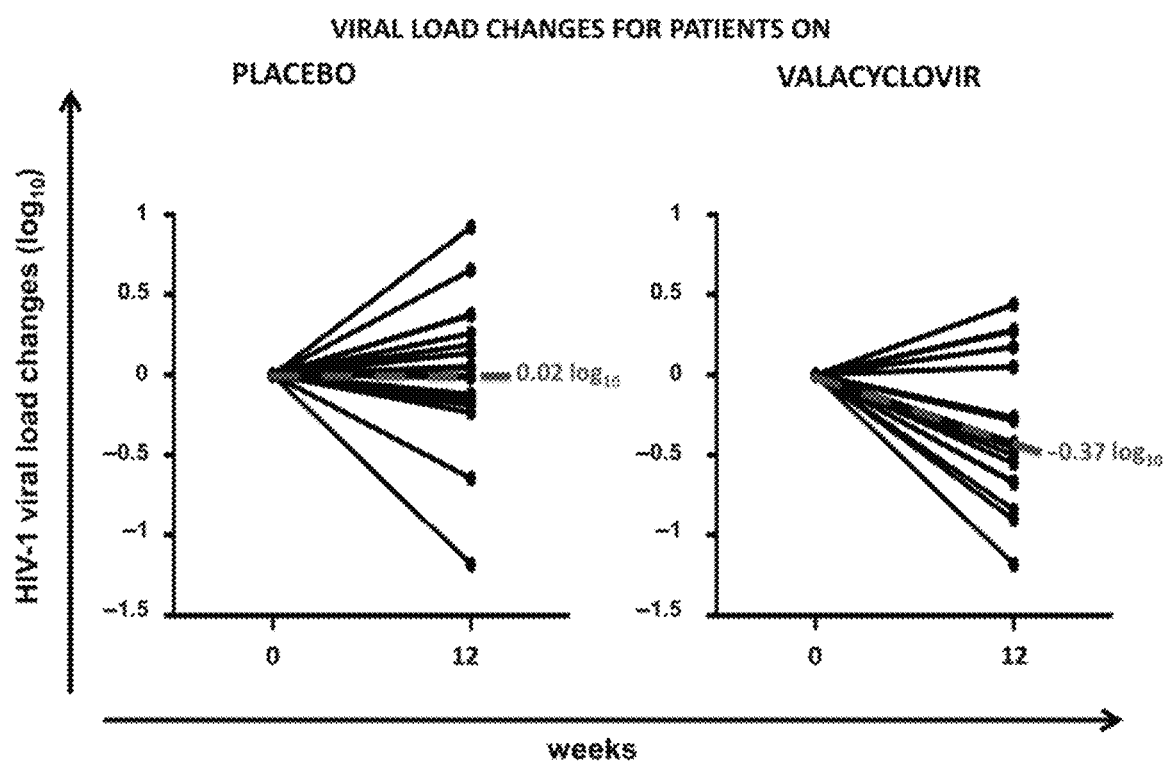
FIG. 2 is a graph depicting the efficacy of prior art HSV suppression drug valacyclovir in regards to reducing the viral load of HIV in patients.

The primary antiviral agent in the therapy is a nucleoside/nucleotide analogs class drug: valacyclovir, famciclovir, acyclovir, pritelivir, or another nucleoside/nucleotide analog class drug documented to reduce herpesvirus replication or acquisition in humans. FIGS. 1 and 2 demonstrate the effects of a nucleoside/nucleotide analogs drug. FIG. 1 is from a study that showed valacyclovir taken once daily reduced the risk of transmission of HSV-2 (Corey et al., 2004). The study followed 1484 monogamous couples consisting of one partner who was clinically symptomatic HSV-2, referred to as the "source partner", and one partner who was susceptible to HSV-2, referred to as the "susceptible partner". Source partners were randomly assigned to take 500 mg of valacyclovir daily or a placebo over a period of 8 months. FIG. 1 shows the frequency of shedding of HSV-2 in the genital tract among source partners taking valacyclovir, of which there were N=39 individuals, as compared with those taking placebo, of which there were N=50 individuals. Over time, the percentage of source partners with HSV-2 shedding taking valacyclovir decreased at a much quicker rate than those taking the placebo. Only those with the placebo had HSV-2 shedding beyond the first 30% of days (Corey et al., 2004). Alternatively, FIG. 2 showed the effects of the HSV drug on HIV. The study from which FIG. 2 was taken observed the viral loads in HIV-1-infected HSV-2-seronegative individuals, some of which were randomly assigned 500 mg of valacyclovir twice daily and others which were assigned a placebo over a period of 12 weeks (Vanpouille et al., 2015). As shown in FIG. 2, the study found that individuals treated with the valacyclovir had HIV-1 viral loads in their plasma that were reduced, on average, by 0.37 $\log_{10}$ copies/mL (Vanpuille et al., 2015). Because of the effects of valacyclovir on both HSV and HIV, as demonstrated by FIGS. 1 and 2 respectively, valacyclovir and other drugs of the same class comprise the primary antiviral agent of the composition.

Figure 3:
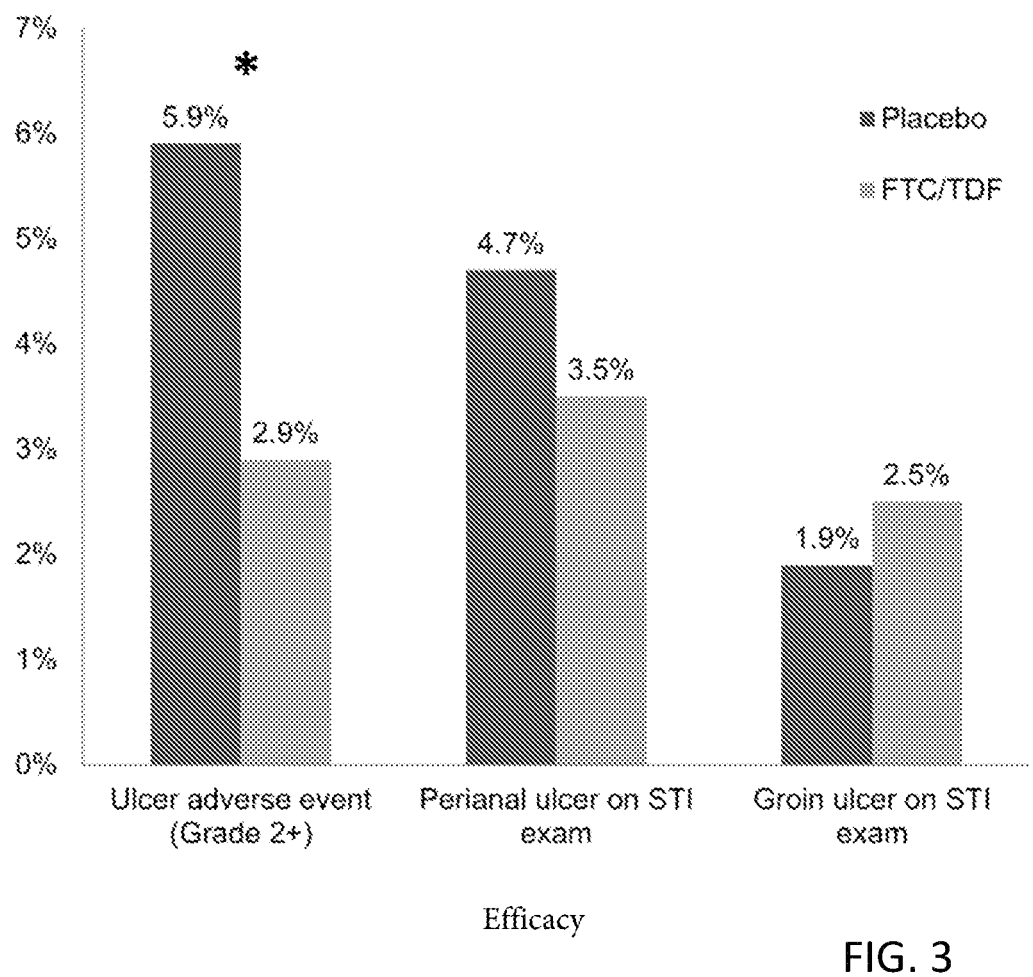
FIG. 3 is a graph depicting the efficacy of prior art HIV prevention drug Truvada in regards to suppressing HSV.

A second antiviral agent is used in the therapy, which can consist of a Nucleoside/Nucleotide Reverse Transcriptase Inhibitor (NRTI) class drug to reduce the likelihood of a DNA polymerase resistance mutation. This antiviral agent may be an NRTI class drug which provides documented cross protection against the herpesvirus family as well as the HIV family. The second antiviral agent may be selected from tenofovir, TDF, TAF, emtricitabine, lamivudine, etc. FIG. 3 demonstrates the efficacy of tenofovir, also known by the brand name Truvada, in suppressing symptoms of HSV-2. Specifically, FIG. 3 shows that tenofovir in daily oral emtricitabine/tenofovir PrEP may reduce the occurrence of ulcers, particularly perianal ulcers, in individuals infected with HSV-2 (Marcus et al., 2014). Utilizing NRTIs that provide cross protection decreases the risk of an HIV and herpes co-infection. Multidrug therapy significantly increases effectiveness for herpesvirus suppression, decreasing the potential for mutation, and preventing HIV acquisition. Several of these antivirals have been shown to reduce herpes viral loads and acquisition risk in clinical studies, although no combinations have been studied beyond TDF and emtricitabine (Celum et al., 2014).

A third drug in the antiviral therapy may consist of another NRTI class drug that mainly targets HIV replication. These drugs include tenofovir, TDF, TAF, emtricitabine, lamivudine, et cetera. This antiviral agent further reduces the patient comorbidity risk of acquiring HIV with an active herpesvirus infection.

The antiviral therapy may include a VP-16 inhibitor, an enzyme that creates mRNA from a virus genome. These inhibitors may include etoposide, or another formulation which has been demonstrated to act against the production of mRNA in herpesviruses.

The antiviral therapy may include an antiviral drug that inhibits virus maturation. These antivirals may include nuclease inhibitor class drugs, enzymes that mature viral DNA for replication. These inhibitors may include emodin, raltegravir, or another nuclease inhibitor which has been demonstrated to interfere with herpesvirus maturation. The antiviral therapy may include a protease inhibitor class drug, an enzyme that matures viral DNA for replication. These inhibitors may include nelfinavir, or another protease inhibitor which has been demonstrated to interfere with herpesvirus maturation. The antiviral cocktail may include alcohols that exhibit antiviral activity against herpes infections, including behenyl alcohol, aliphatic alcohol, or another formulation which acts against lipid envelopes of herpesviruses.

Use of multiple antiviral agents allow for synergistic effects between each component of the cocktail. That is, less of each antiviral agent may be used when in combination therapy to achieve the same result, in this case herpes suppression. This facet, added with the decreased likelihood for resistance mutations, means multiple antiviral agents are critical for the effectiveness of the therapy.

FIGS. 4-7 illustrate dosage schedules and measurement methods for proposed clinical trials showing how to measure the effectiveness of the novel antiviral cocktail. The primary hypothesis is that the novel antiviral cocktail effectively suppresses herpes viral loads while protecting against an HIV acquisition. The relevant subjects are those who are HIV negative and herpesvirus positive.

All participants will be screened to be HIV negative and herpesvirus positive via blood sample. Patients must be sexually active. Patients halt any antiviral therapy for a duration prior to beginning the trial. Patients will be monitored intermittently on antiviral therapy for a period up to 28 weeks (example for a period of 4, 8, or 12 weeks). One or more of the primary experimental groups shown in FIG. 4 will be considered for this trial. All therapies are orally administered once daily. Each dose may be administered as one or two tablets containing the three drugs. In a different trial, only experimental group 3 would be considered, and optionally either control 1 or group 2, for example in a pharmacokinetics (PK) and safety study.

FIG. 5 describes one or more tests that could be performed on all subjects, their frequency, and metrics of success.

It is expected that none of the participants in group 3 of FIG. 4 with sufficient medication adherence should seroconvert from HIV negative to HIV positive for the duration of the therapy. Blood drug levels for PK may also be tested. From previous research, group 1 may expect an HSV PCR detectability rate median of 20 percent of days (Ramchandani et al., 2016). Group 2, in the case of 500 mg valacyclovir, may expect an HSV PCR detectability rate median of 5 percent of days (Wald et al., 2016). Group 3's HSV detectability rate median must be lower than 5 percent to imply benefit over existing therapies. If group 3's HSV PCR detectability rate median is at or near 0 percent, a negative western blot test may further indicate viral suppression to undetectable levels. This low or undetectable viral load would imply significantly reduced transmission potential. All participants in groups 2 and 3 may be filtered for medication adherence by tenofovir hair sample results (Liu et al., 2014).

Similar to ongoing PrEP 2-1-1 studies, this invention could be adapted for short term contact events. The therapy can be administered at very frequent intervals for high-risk contact events short in duration. These intervals include twice daily, daily, or at a more frequent interval. These contact events may include brief periods of exposure between humans, planned sexual activity, childbirth, contact with wild animals, captive animals, or any event where an HIV negative, herpes positive human is at risk to transmit their infection to another human or mammal. Effective short-term therapy will include administering the antivirals through aforementioned delivery means, and at frequent intervals. The effect of the frequent antiviral administration is that herpes viral replication is temporarily blocked in the patient, and viral transmission risk from the infected patient is significantly reduced. Simultaneously, HIV infection risk to the patient will be reduced due to the short-term administration of antivirals.

The proposed clinical trial of FIG. 6 demonstrates a way to validate the antiviral cocktail for short term exposure therapy. The primary hypothesis is that the novel antiviral cocktail may still offer high levels of protection against HIV acquisition (with the possibility of temporary herpes suppression), even when not taken as a daily therapy.

All participants will be screened to be HIV negative and herpesvirus positive via blood sample. Patients must be sexually active (example have a nonzero level of sexual activity). Patients halt any antiviral therapy for a duration prior to beginning the trial. Patients will be monitored intermittently on antiviral therapy for a period up to 28 weeks (example for a period of 4, 8, or 12 weeks). Patients will be monitored on antiviral therapy in a "2-1-1" schedule. A double dosage will be taken 2-24 hours prior to exposure, one dose will be taken 24 hours after exposure, and one additional dose will be taken 48 hours after exposure. One or more of the following primary experimental groups will be considered for this trial.

FIG. 7 describes the tests performed on all subjects, their frequency, and metrics of success.

It is expected that none of the participants in group 3 of FIG. 6 with sufficient medication adherence should seroconvert from HIV negative to HIV positive for the duration of the therapy. During 2-1-1 therapy, the herpesvirus load is measured. A low or undetectable viral load would imply significantly reduced transmission potential, despite participants not being on daily suppressive therapy. All participants in groups 2 and 3 may be filtered for regimen adherence by tenofovir or valacyclovir/pritelivir hair sample results.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A pharmaceutical composition for inhibiting an HIV infection and suppressing a herpes infection in an HIV-seronegative HSV-seropositive subject,
    consisting of (a) valacyclovir, tenofovir, and etoposide; (b) valacyclovir, tenofovir, and emodin; or (c) valacyclovir, tenofovir, and nelfinavir, and optionally at least one alcohol:
    wherein the composition is used for inhibiting resistance mutations while obstructing replication at phases of the viral reproductive process.

2. The composition of claim 1, wherein the at least one alcohol is at least one of behenyl alcohol or aliphatic alcohol.

* * * * *